March 24, 1964 R. S. MOORE Plant Pat. 2,381
ROSE
Filed Dec. 18, 1961
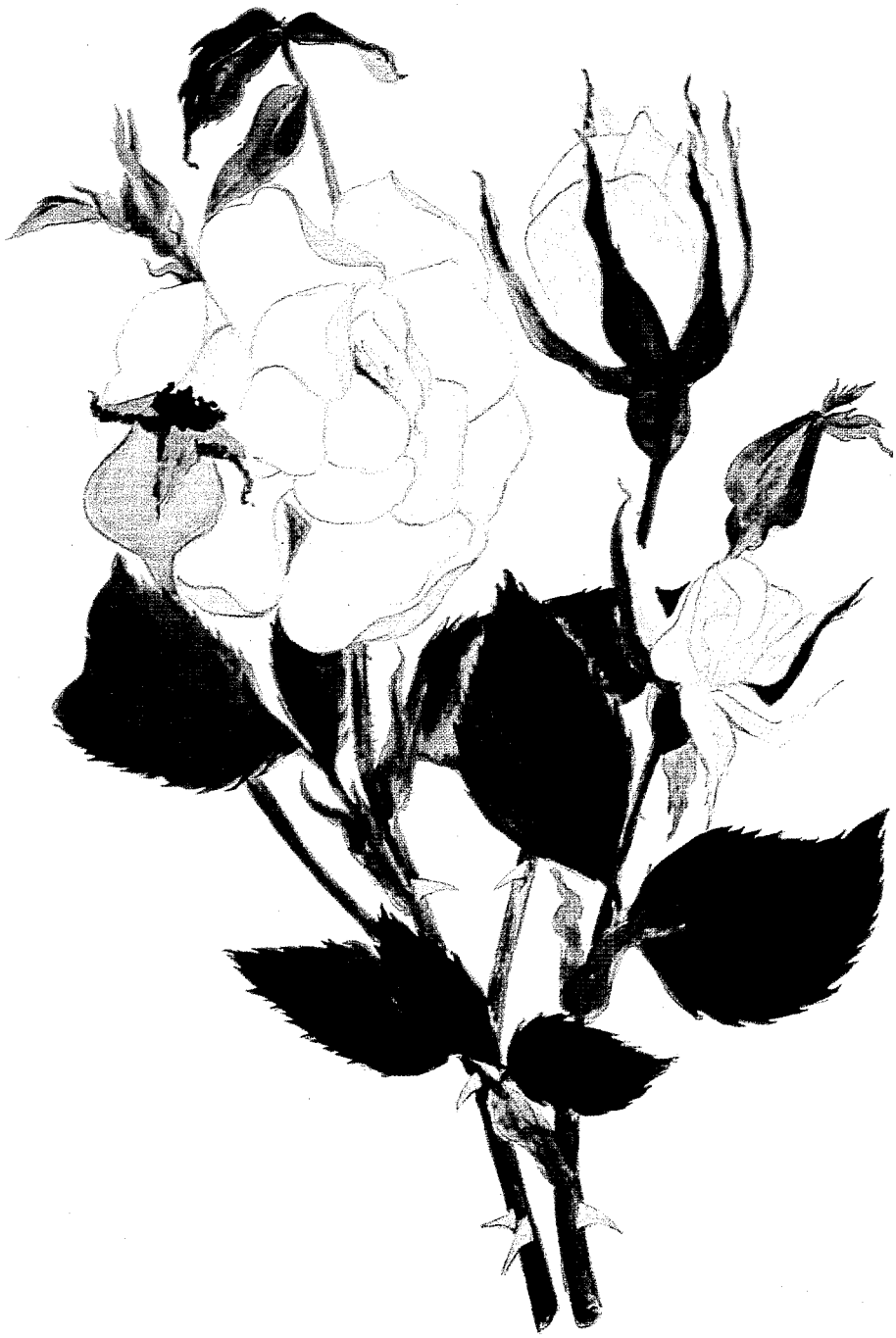
WITNESS
Jeanette Nunn Copley
INVENTOR
RALPH S. MOORE
ATTORNEYS
By Eckhoff & Sliss United States Patent Office Plant Pat. 2,381
Patented Mar. 24, 1964

2,381
ROSE

Ralph S. Moore, 2519 E. Mineral King, Visalia, Calif.

Filed Dec. 18, 1961, Ser. No. 160,378
1 Claim. (Cl. Plt.—11)

This invention relates to a new and distinct variety of tall, bush-type hybrid tea rose plant.

This plant is characterized as to novelty by its strong, vigorous growth habit and large glossy foliage, plus the unique orange (sometimes almost brownish tints) coloring of the flower.

This hybrid tea rose variety resembles Mojave (U.S. Plant Patent 1,176) in flower form and color. The foliage and plant habit resemble Sutter's Gold (U.S. Plant Patent 885). The plant is healthy and vigorous, with abundant foliage. It makes an excellent tree rose when budded high for this purpose. It breaks into new growth quickly.

The budding eyes are plump and easily handled for propagation purposes. The flowers and buds have good form and come on stems sufficiently long for cutting and arranging. The healthy foliage of the plant minimizes the care needed to keep the plant well-groomed and minimizes the need for fungicidal spray.

The instant variety of hybrid tea rose plant was originated by me, in my nursery located at Visalia, California, and under conditions of careful control and observation, as a cross between Sister Therese (hybrid tea) (not patented) as the seed parent and Lucia Zuloaga (hybrid tea) (not patented) as the pollen parent. Subsequent to origination of the variety, I successfully asexually reproduced it in my nursery, located as aforesaid, by budding as well as cuttings; the reproductions having run true in all respects.

The drawing illustrates a spray including foliage, buds and flowers.

Referring now specifically to the new and distinct variety of hybrid tea rose plant, the following is a detailed description thereof in outline; all major color plate identifications being to the British Colour Council Horticultural Colour Chart, except where common terms of color definition are employed.

Type: Tall; bush; outdoor; seedling; cut flowers; garden decoration.
Class: Hybrid tea.

*Flowers*

Continuity: Intermittent.
Fragrance: Moderate.
Flowers borne: Singly on strong, medium length stems. Sometimes on strong shoots flowers come in candelabra manner as does parent, Sister Therese.
Quantity of bloom: Free, outdoors.
Bud:
*Peduncle.*—Medium length; medium heavy; erect; green; smooth.
*Before calyx breaks.*—Size—large. Form—long; pointed; without foliaceous appendages on the surface of the bud; foliaceous parts extending beyond the tip of the bud equal to one-fourth or more of its length. Color—green.
*As calyx breaks.*—Color—red-orange.
*As first petal opens.*—Size—large. Form—pointed. Color: outside—Lemon Yellow 4/1 at base shading into yellow overlaid with Shrimp Red 6/6 to give orange-red effect; inside—same as outside except with veins of a deeper shade. Opening—opens well at all times.
Bloom:
*Size when fully opened.*—Large, 4" to 5".
*Petalage.*—Double, with from 18 to 20 petals arranged regularly.

*Form.*—High center with open cup at first, becoming more open, petals remaining at first loosely rolled outward, becoming later at maturity very loosely rolled outward.
Petals: Leathery, with inside satiny; outside satiny.
*Shape.*—Outside—obovate. Intermediate—obovate. Inside—obovate or spatulate.
*Color.*—Newly opened flower from plant grown outdoors (September)—Outside petal: outside and inside surfaces—Buttercup Yellow 5/1 at base blending into Marigold Orange 11/2. Intermediate petal: outside surface—same as outside petal; inside petal—Buttercup Yellow 5/1 at base blending into Saturn Red 13/2. Inner petal: outside surface—Buttercup Yellow 5/11 at base blending into Saturn Red 13/2; inside surface—Buttercup Yellow 5/11 blending into Orpiment Orange between 10/1 and 10/2. All of the above shades of red and orange are modified by overlaying and blending with the yellow undercolor. A flower that was open for three days outdoors in September had outside and inside petals similar to the above but with slightly lighter shades.
*General color effect.*—Newly opened flower—bright orange or red orange. Three days open—orange is toned down lightly with some pink.
*Behavior.*—Drop off cleanly. The flowers open well and have a richer color in cool weather and fade faster in hot weather.
Flower longevity (September): Three to four days on bush in the garden. Two or three days as cut roses kept at living room temperature after having been grown and cut outdoors.
Reproductive organs:
*Stamens.*—Many; arranged regularly.
*Filaments.*—Medium; yellow; most with anthers.
*Anthers.*—Medium large; yellow; open all at once.
*Pollen.*—Moderate to abundant; yellow.
*Pistils.*—Medium number.
*Styles.*—Uneven; medium; red; medium; loosely bunched.
*Stigma.*—Yellow.
*Ovaries.*—All enclosed in calyx.
*Hips.*—Short; globular; yellow.
*Sepals.*—Permanent; moderate; spear-shaped; curled; brown.
*Seeds.*—Few; of medium size.

*Plant*

Foliage:
*Leaves.*—Compound of three to five leaflets; abundant; very large; heavy; leathery; glossy.
*Leaflets.* — Shape — oval. Apex — acute. Base—round. Margin—serrate. Color: mature—upper surface normal green; under surface normal green; young—upper surface normal green; under surface normal green with light tint of red in veins. Rachis—medium heavy; under side sparsely thorny; upper side grooved; lightly hairy. Stipules—medium long; wide; medium points turning out at an angle of less than 45°. Disease—resistant to mildew and seems to be resistant to blackspot as compared with other varieties grown under comparable cultural conditions at Visalia, California.
Growth:
*Habit.*—Bushy; upright; much branched.
*Growth.*—Free; vigorous.
*Canes.*—Medium to heavy.
*Main stems.*—Color—green with some brown. Thorns—several; medium to long with short oval base; hooked only slightly downward. Prickles—few to none. Hairs—none.

*Branches.*—Color—green. Thorns—few; short to medium; hooked only slightly downward. Prickles—few to none. Hairs—none.

*New shoots.*—Color—bright green sometimes tinted with bronze. Thorns—few; hooked only slightly downward. Prickles—none. Hairs—none.

The following is claimed:

A new and distinct variety of hybrid tea rose plant, substantially as herein shown and described, of the tall, bush-type, outdoor variety characterized by vigorous growth habits with budding eyes which are plump and easily handled for propagation, by healthy foliage minimizing the care necessary to properly raise the plant, by large leathery petals arranged regularly and being buttercup yellow at the base, blending into marigold orange, said flower resembling Mojave in form and color with a plant habit and foliage resembling Sutter's Gold.

No references cited.